United States Patent [19]

Stulen

[11] 4,213,466
[45] Jul. 22, 1980

[54] MONITORING MYOELECTRIC SIGNALS

[75] Inventor: Foster B. Stulen, Somerville, Mass.

[73] Assignee: Harvard College, President and Fellows, Cambridge, Mass.

[21] Appl. No.: 933,071

[22] Filed: Aug. 11, 1978

[51] Int. Cl.² .............................................. A61B 5/05
[52] U.S. Cl. .................................................. 128/733
[58] Field of Search .................... 128/733; 307/233 R; 324/78 F; 328/167; 330/109

[56] References Cited

U.S. PATENT DOCUMENTS

| | | | |
|---|---|---|---|
| 3,304,505 | 2/1967 | Prider | 307/233 |
| 3,638,037 | 1/1972 | McMurtrie | 328/167 |
| 3,978,847 | 9/1976 | Fehnio et al. | 128/733 |
| 4,045,731 | 8/1977 | Tokunou et al. | 328/167 |
| 4,063,450 | 12/1977 | Lyons | 328/167 |
| 4,136,314 | 1/1979 | Blackmer et al. | 328/167 |

OTHER PUBLICATIONS

DeLuca, C. J. et al., "A Polar Technique for Displaying EMG Signals", 28th ACEMB, New Orleans, La., Sep. 20–24, 1975.

*Primary Examiner*—Robert W. Michell
*Assistant Examiner*—Francis J. Jaworski

[57] ABSTRACT

A muscle fatigue monitor featuring detecting a myoelectric signal and providing a first output signal representative of said myoelectric signal, producing a second output signal corresponding to a portion of said first output signal having components in a selected frequency band, providing a control signal corresponding to the difference in magnitude between said output signals, varying the magnitude of said second signal in accordance with the value of said control signal, and displaying the variation in the frequency spectrum of said myoelectric signal as a function of time.

1 Claim, 1 Drawing Figure

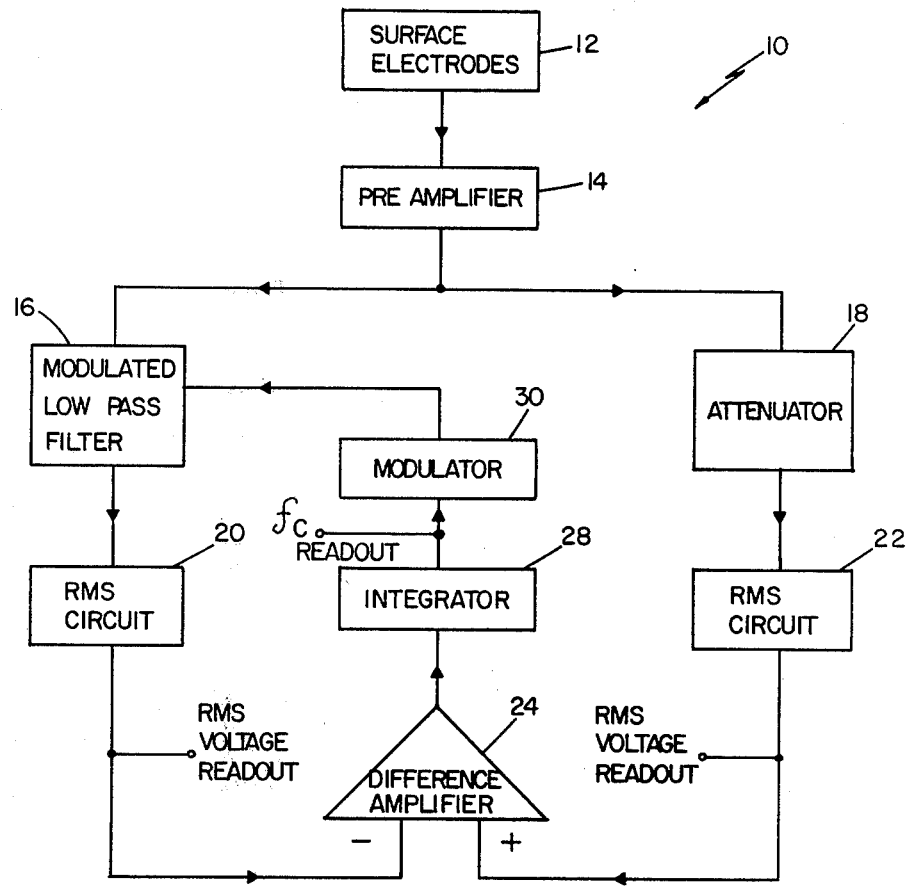

MONITORING MYOELECTRIC SIGNALS

BACKGROUND OF THE INVENTION

This invention relates to continuously measuring the frequency of myoelectric signals.

In a U.S. patent application Ser. No. 933,072 entitled "Muscle Fatigue Monitor" recently filed by Foster B. Stulen and Carlo J. Deluca (hereby incorporated by reference), there is disclosed Stulen's and DeLuca's joint invention, conceived prior to mine, in which the changing frequency of a myoelectric signal is monitored by using low pass and high pass filters to divide the signal at a cutoff frequency, and, based on the magnitude of the difference between the divided signals, generating a control signal which varies the cutoff frequency so as to reduce that difference. The changing cutoff frequency or the difference in the divided signals can be displayed as a function of time.

SUMMARY OF THE INVENTION

In general, the invention features detecting a myoelectric signal and providing a first output signal representative of said myoelectric signal, producing a second output signal corresponding to a portion of said first output signal having components in a selected frequency band, providing a control signal corresponding to the difference in magnitude between said output signals, varying the magnitude of said second signal in accordance with the value of said control signal, and displaying the variation in the frequency spectrum of said myoelectric signal as a function of time.

In preferred embodiments the first output signal is low pass filtered to produce the second, and the output signals are scaled prior to generation of the control signal.

The invention provides accurate monitoring, with efficent use of circuitry.

DESCRIPTION OF PREFERRED EMBODIMENT

We turn now to the circuitry and operation of a preferred embodiment of the invention, after first briefly describing the drawings.

DRAWINGS

The FIGURE is a block diagram of the circuitry embodying this invention.

CIRCUITRY

Referring to the FIGURE, the muscle fatigue monitor circuit is shown generally at 10. A myoelectric signal is detected by differential surface electrodes 12 and transmitted to preamplifier 14. Preamplifier 14 first filters the myoelectric signal to remove noise and low frequency artifacts caused by body movements and then amplifies the signal.

The output from preamplifier 14 is fed to a modulated low pass filter 16. The filter 16 is the same as the low pass filter of the incorporated Stulen and DeLuca patent application. Each stage is the same as shown in FIG. 2 of that application and operates in the same manner.

The signal from preamplifier 14 is also fed to attenuator 18 which alters the signal value by a factor of $\sqrt{\frac{1}{2}}$.

The signals from filter 16 and attenuator 18 are fed into identical RMS circuits 20, 22, which calculate true rms voltage. RMS circuits 20, 22 are of the same type as those in the incorporated reference and continuously send out rms voltages corresponding to the magnitudes of the input signals they receive.

The RMS outputs are fed to difference amplifier 24, the output of which is proportional to the difference between its two rms voltage inputs.

The output of amplifier 24 is then received by integrator 28 which produces a slowly varying D.C. voltage corresponding to the integral of the differences between the low-filtered and the attenuated rms voltages.

The integrated output is fed to modulator 30. The output of modulator 30 is a pulse width modulated (PWM) signal or pulse train, the pulse width of which increases or decreases with a corresponding change in the level of the integrator output signal. The PWM signal is then fed back to filter 16.

OPERATION

Referring to the FIGURE, surface electrodes 12 are connected to the patient's muscle, and an initial cutoff frequency is preset for filter 16. This selected frequency is usually about 90 Hz, which is in the midrange of possible initial median frequencies.

When the monitor is activated, the actual myoelectric signal is sensed by electrodes 12 and sent through preamplifier 14 to filter 16 and attenuator 18. Attenuator 18 receives the entire preamplified signal and converts it to an output signal which is approximately equal to the output of filter 16 when the filter's cutoff frequency is the same as the actual median frequency of the myoelectric signal. If the actual median frequency is above or below the selected cutoff frequency, the filter's and the attenuator's rms voltages from RMS circuits 20, 22 will not be the same. When the rms difference is zero the cutoff frequency approximately equals the true median frequency.

The different rms voltages are fed into amplifier 24. The amplifier output represents the difference between the rms voltages. If the filter output is greater than the attenuator output, the output of the difference amplifier 24 has a negative value. If the opposite were the case, the amplifier output would be positive. This signal is received by integrator 28. Integrator 28 then produces a slowly varying D.C. signal which is fed to modulator 30.

The modulator 30 combines the integrator output with a triangle wave to produce a pulse train which is fed to the filter 16. The filter's cutoff frequency directly depends on the pulse width of the signal from the modulator, and the level of the integrator output determines this pulse width.

Based on the pulse width of the modulator output signal, the filtered cutoff frequency increases or decreases toward the actual median frequency. The rms voltages are compared again and the difference is less. Integrator 28 adds the new difference to the old, and the cutoff frequency is increased or decreased again towards the real median. This is a continuous process which forces the cutoff frequency toward close approximation of the true median frequency. In the event the modulator output raises or lowers the filter's cutoff frequency past the actual median, the output of difference amplifier 24 will change sign. The new output will reduce the integrator output thereby correcting the overshoot.

The monitor can operate in a track mode in which the filter's cutoff frequency is continually displayed as it decreases with muscle fatigue. The decrease in frequency can be real-time recorded in this manner and directly observed as it occurs.

The monitor can also function in a hold mode if the modulator output is disabled after the cutoff frequency initially approximates the actual median frequency. Disabling can be accomplished by a switch (not shown) breaking the input to difference amplifier 24, integrator 28 or modulator 30. In this mode of operation, disabling the modulator 30 after the rms voltages are balanced fixes the filter's cutoff frequency at this initial median frequency. The median frequency of the myoelectric signal decreases as the muscle is fatigued, however, and the filter passes increasingly more of the entire signal. The resulting difference in the outputs of RMS circuits 20, 22 can be displayed and recorded.

What is claimed is:

1. In a neurological monitor for measuring the spectral variation in a myoelectric signal, said monitor being of the type including
   an electrode suitable for contacting a living being and detecting said myoelectric signal,
   circuitry for processing said myoelectrical signal to provide a display signal representative of said spectral variation, said circuitry comprising
   means for amplifying said myoelectric signal to provide an amplified signal,
   filter means for providing a filtered signal corresponding to a portion of said amplified signal having frequency components on one side of a variable cutoff frequency,
   means for comparing said filtered signal to a reference signal and providing a control signal that is dependent on the difference in magnitude between said filtered and reference signals,
   means for automatically varying said cutoff frequency in accordance with the value of said control signal,
   means for providing a display signal representitive of said spectral variation in said myoelectric signal, and
a display driven by said display signal, for observing said spectral variation in said myoelectric signal,
the improvement comprising an attenuator for receiving said amplified signal and producing said reference signal, the attenuation being selected to make the magnitudes of said reference and filtered signals equal when said cutoff frequency is set at a median frequency of said myoelectric signal,
whereby said circuitry will tend to adjust said cutoff frequency to said median frequency.

* * * * *